United States Patent [19]
Wall et al.

[11] Patent Number: 5,180,722
[45] Date of Patent: * Jan. 19, 1993

[54] 10,11-METHYLENEDIOXY-20(RS)-CAMP-TOTHECIN AND 10,11-METHYLENEDIOXY-20(S)-CAMP-TOTHECIN ANALOGS

[75] Inventors: Monroe E. Wall, Chapel Hill; Mansukh C. Wani, Durham; Allan W. Nicholas; Govindarajan Manikumar, both of Raleigh, all of N.C.

[73] Assignee: Research Triangle Institute, Research Triangle Park, N.C.

[ * ] Notice: The portion of the term of this patent subsequent to Jan. 16, 2007 has been disclaimed.

[21] Appl. No.: 581,916

[22] Filed: Sep. 13, 1990

Related U.S. Application Data

[63] Continuation-in-part of Ser. No. 407,779, Sep. 15, 1989, Pat. No. 5,049,668, and a continuation-in-part of Ser. No. 511,953, Apr. 17, 1990, Pat. No. 5,053,572, which is a continuation of Ser. No. 38,157, Apr. 14, 1987, abandoned.

[51] Int. Cl.$^5$ .................... A61K 31/47; C07D 491/22
[52] U.S. Cl. .................... 514/219; 514/253; 514/279; 514/283; 540/481; 540/597; 544/361; 546/41; 546/48
[58] Field of Search .................... 546/41, 48; 540/481, 540/597; 514/219, 253, 279, 283

[56] References Cited

U.S. PATENT DOCUMENTS 4,031,986 6/1977 Sugasawa .................... 546/48

(List continued on next page.)

FOREIGN PATENT DOCUMENTS 0074256 3/1983 European Pat. Off. .

(List continued on next page.)

OTHER PUBLICATIONS

Yang, et al. (AR13), Chemical Abstracts, vol. 100: 139434w (1984).

(List continued on next page.)

*Primary Examiner*—Diana G. Rivers
*Attorney, Agent, or Firm*—Oblon, Spivak, McClelland, Maier & Neustadt

[57] ABSTRACT

A camptothecin analog having the structure shown below:

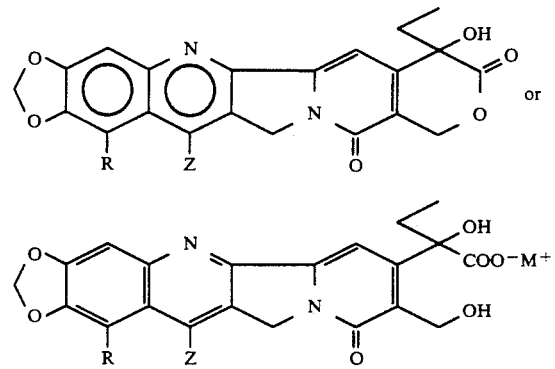

where Z is H or $C_{1-8}$ alkyl and R is $NO_2$, $NH_2$, $N_3$, hydrogen, halogen, COOH, OH, O—$C_{1-3}$ alkyl, SH, S—$C_{1-3}$ alkyl, CN, $CH_2NH_2$, NH—$C_{1-3}$ alkyl, $CH_2$—NH—$C_{1-3}$ alkyl, N($C_{1-3}$ alkyl)$_2$, $CH_2N(C_{1-3}$ alkyl)$_2$, O—, NH—, or S—$CH_2CH_2N(CH_2CH_2OH)_2$, O—, NH— or S— $CH_2CH_2CH_2N(CH_2CH_2OH)_2$, O—, NH— or S—$CH_2CH_2N(CH_2CH_2OH)_2$, O—, NH— or S—$CH_2CH_2CH_2N(CH_2CH_2CH_2OH)_2$, O—, NH— or S—$CH_2CH_2N(C_{1-3}$ alkyl)$_2$, O—, NH— or S—$CH_2CH_2CH_2N(C_{1-3}$ alkyl)$_2$, CHO, $C_{1-3}$ alkyl or $NHCOCHR^1NR^2R^3$, where $R^1$ is the side-chain of an α-amino acid and $R^2$ and $R^3$, independently are hydrogen or a lower alkyl group or $R^3$ is a peptide unit containing 1-3 amino acid units bonded to the nitrogen through a peptide bond; NHCO—$C_{2-8}$-alkylene—X or NHCO—$C_{2-8}$-alkenylene—X, where X is COOH; $CONR^2$—$(CH_2)_n$—$NR^2R^3$, where n=1-10 and $R^2$ and $R^3$ are as defined above; NHCO—B—$(CH_2)_n$—$NR^2R^3$, where B=oxygen or NH, or

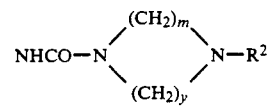

where m+y=3-6, and salts thereof.

30 Claims, 1 Drawing Sheet

U.S. PATENT DOCUMENTS

| | | |
|---|---|---|
| 4,473,692 | 9/1984 | Miyasaka et al. ............... 546/48 |
| 4,545,880 | 10/1985 | Miyasaka et al. ............... 546/48 X |
| 4,604,463 | 8/1986 | Miyasaka et al. ............... 544/125 |
| 4,894,456 | 1/1990 | Wall et al. ............... 546/41 |
| 4,914,205 | 4/1990 | Sawada et al. ............... 546/70 |
| 4,981,968 | 1/1991 | Wall et al. ............... 544/361 |
| 5,049,668 | 9/1991 | Wall et al. ............... 540/481 |
| 5,053,512 | 10/1991 | Wani et al. ............... 546/41 |
| 5,106,742 | 4/1992 | Wall et al. ............... 435/233 |

FOREIGN PATENT DOCUMENTS

| | | |
|---|---|---|
| 0220601 | 5/1987 | European Pat. Off. |
| 321122 | 6/1989 | European Pat. Off. |
| 57-116015 | 7/1982 | Japan . |
| 59-05188 | 1/1984 | Japan . |
| 59-46284 | 3/1984 | Japan . |
| 59-51287 | 3/1984 | Japan . |
| 59-51289 | 3/1984 | Japan . |
| 61-50985 | 3/1986 | Japan . |
| 61-85319 | 4/1986 | Japan . |
| 61-85389 | 4/1986 | Japan . |

OTHER PUBLICATIONS

Pan, et al. (AR14), Chemical Abstracts, vol. 84: 115629p (1976).

Wani, et al. J. Med. Chem., vol. 29, No. 11, pp. 2358-2363 (1986).

Wall, et al., J. Am. Chem. Soc., vol. 88, No. 16, pp. 3888-3890 (1966).

*Cancer Research*, (1989), vol. 49, 4385-5489, "DNA Topoisomerase I-Meditated DNA Cleavage and Cytotixicity of Camptothecin Analogues", Hisang et al.

*Cancer Research*, (1989), vol. 49, 1465-1469, "Structure-Activity Study of the Actions of Camptothecin Derivatives on Mammalian Topoisomerase I . . . " Jaxel et al.

*The Journal of Biological Chemistry*, (1985, 260, 14873-14878, "Camptothecin Induces Protein-Linked DNA Breaks Via Mammalian DNA Topoisomerase I" Hsiang et al.

*J. Med. Chem*, (1980), 23, 544-560, "Plant Antitumor Agents. 18.[1] Synthesis and Biological Activity of Camptothecin Analogues", Wani et al.

*J. Med. Chem*, (1986), 29, 1553-1555, "Plant Antitumor Agents 22.[1] Isolation of 11-Hydroxycamptothecin from *Camptotheca acuminata* Decne . . . " Wall et al.

*Journal of Labelled Compounds and Radiopharmaceuticals*, (1981), 18, 319-329, "The Preparation of Tritium and Deuterium-Labelled Camptothecin", Ronman et al.

*J. Medicinal Chemistry*, (1987), 30, 1774-1779, "Plant Antitumor Agents 25.[1] Total Synthesis and Antileukemic Activity of Ring A . . . ", Wani et al.

*J. Medicinal Chemistry*, (1990), 33, 972-978, "Plant Antitumor Agents. 29.[1] Synthesis and Biological Activity of Ring D and Ring 3 . . . " Nicholas et al.

*J. Org. Chem.* (1974), 39, 303-311, "Synthesis of Some DE and CDE Ring Analogs of Camptothecin", Plattner et al.

*J. of Am. Chem. Soc.* (1972), 94, 8615, "Synthesis of Some DE and CDE Ring Analogs of Camptothecin" Plattner et al.

*J. Org. Chem.*, (1974), 39, 3430-3432, "Synthesis of Biological Evaluation of De-AB-Camptothecin", Danishefsky et al.

Govindachari et al, "9-Methoxycamptothecin. A New Alkaloid From *Mappia foetida* Miers" Indian J. Chem. vol. 110(4), 453-454 (1972).

*Proc. Annu. Meet. Am Assoc. Cancer Res*, (1988), 29, A1080, "Structure-Activity Study of the Relation Between Topoisomerase I Inhibition and Antitumor . . . " Abstract.

*Proc. Annu. Meet. Am Assoc. Cancer Res*, (1989), 8, A1019, "A Clinical Study of a Camptothecin Derivative, CPT-11 on Hematological Malignancies", (Mtg Abstract).

*Proc. Ann. Meet. Am Assoc. Cancer Res*, (1989), 30, A2485, "Irreversible Trapping of the DNA-Topoisomerase I Covalent Complex and Affinity Labeling of . . . " Abstract.

*J. Med. Chem*, (1989), 32, 715-720, "Modification of the Hydroxy Lactone Ring of Camptothecin: Inhibition of Mammalian Topoisomerase I and . . . ", Mong et al. Abstract.

*Science*, (1989), 246, 1046-1048, "DNA Topoisomerase I-Targeted Chemotherapy of Human Colon Cancer in Xenografts", Giovanella et al.

*Proc. Annu. Meet Am. Assoc. Cancer Res.*, (1989), A2476, "Structure-Activity Studies of 20(S)-Captothecin Analogs" (Meeting Abstract).

CAMPTOTHECIN (CPT)

CPT-SODIUM SALT 10,11-MDO-20(RS)-CPT

9-AMINO-10,11-MDO-20(RS)-CPT

9-GLYCINAMIDO-10,11-MDO-20(RS)-CPT HYDROCHLORIDE 10-11-MDO-20(RS)-CPT-SODIUM SALT

*FIG. 1*

10,11-METHYLENEDIOXY-20(RS)-CAMPTOTHECIN AND 10,11-METHYLENEDIOXY-20(S)-CAMPTOTHECIN ANALOGS

This application is a Continuation-in-Part of U.S. patent application No. 07/407,779 filed Sep. 15 1989, now U.S. Pat. No. 5,049,668, and a Continuation-in-Part of U.S patent application No. 07/511,953, filed Apr. 17, 1990 now U.S. Pat. No. 5,053,512, a continuation of U.S. patent application No. 07/038,157 filed Apr. 14, 1987 now abandoned, both of which are incorporated-herein-by-reference in their entirety

BACKGROUND OF THE INVENTION

1. Field of the Invention

The present invention relates to camptothecin analogs which are useful as antitumor agents. More specifically, the invention is directed to water-insoluble and water-soluble derivatives of 10,11-methylenedioxy-20(RS)-camptothecin and 10,11-methylenedioxy-20(S)-camptothecin. These compounds are collectively referred to as 10,11-MDOCPT below.

2. Discussion of the Background

Camptothecin is a pentacyclic alkaloid initially isolated from the wood and bark of Camptotheca acuminata by Wall et al (M. E. Wall, M. C. Wani, C. E. Cook, K. H. Palmer, A. T. McPhail, and G. A. Sim, J. Am. Chem. Soc., 94:388 (1966)).

Camptothecin is highly biologically active and displays strong inhibitory activity toward the biosynthesis of nucleic acids. Additionally, camptothecin exhibits potent antitumor activity against experimentally transplanted carcinoma such as leukemia L-1210 in mice or Walker 256 tumor in rats.

Several methods for the synthesis of camptothecin and camptothecin analogs are known. These synthetic methods include (i) methods in which naturally occurring camptothecin is synthetically modified to produce a number of analogs and (ii) totally synthetic methods.

U.S. Pat. Nos. 4,604,463; 4,545,880; and 4,473,692 as well as European Patent Application 0074256 are examples of the former type of synthetic strategy. Additional examples of this strategy can be found in Japanese Patents 84/46,284; 84/51,287; and 82/116,015. These methods require naturally occurring camptothecin which is difficult to isolate and hence these methods are not suitable for the production of large quantities of camptothecin or analogs.

Examples of a variety of totally synthetic routes to camptothecin and camptothecin analogs can be found in the following references: Sci. Sin. (Engl. Ed), 21(1), 87-98 (1978); Fitoterpapia, 45(3), 87-101 (1974); Yakugaku Zashi, 92(6), 743-6 (1972); J. Org. Chem., 40(14), 2140-1 (1975); Hua Hsueh Hsueh Pao, 39(2), 171-8 (1981); J. Chem. Soc., Perkin Trans 1, (5) 1563-8 (1981); Heterocycles, 14(7), 951-3 (1980); J. Amer. Chem. Soc., 94(10), 3631-2 (1972); J. Chem. Soc. D, (7), 404 (1970) and U.S. Pat. No. 4,031,098.

Synthetic studies directed to camptothecin analogs have also been conducted by the present inventors and are disclosed in J. Med. Chem., 23(5), 554-560 (1980); J. Med. Chem., 29(8), 1553-1555 (1986) and J. Med. Chem., 29(11), 2358-2363(1986) for example.

Water-solubility is an important criterion in developing potential antitumor compounds for pharmaceutical use. Most camptothecin analogs known in the art have relatively poor water-solubility. A need exists for additional camptothecin compounds showing high antitumor activity and for water-soluble camptothecin analogs and methods for preparing the same.

SUMMARY OF THE INVENTION

Accordingly, one object of the present invention is to provide camptothecin analogs containing the 10,11-methylenedioxy moiety.

A further object is to provide camptothecin analogs which exhibit high cytotoxic activity and which can be readily prepared.

These and other objects which will become apparent from the following specification have been achieved by the process of the present invention and the compounds produced thereby.

More specifically, the invention is directed to compounds which are derivatives of 10,11-methylenedioxy-20(RS)-camptothecin (also called 10,11-MDO-20(RS)-CPT) and 10,11-methylenedioxy-20(S)-camptothecin (also called 10,11-MDO-20(S)-CPT) which are highly active camptothecin analogs.

BRIEF DESCRIPTION OF THE DRAWING

A more complete appreciation of the invention and many of the attendant advantages thereof will be obtained as the same becomes better understood by reference of the following detailed description when considered in connection with the accompanying drawing, wherein.

Detailed Description of the Preferred Embodiments 10,11-MDO-20(S)-CPT is an extremely potent camptothecin analog and is one of the most potent inhibitors of the enzyme topoisomerase I known. 10,11-MDO-20(S)-CPT is highly active in such in vitro cytotoxicity tests as the 9KB and 9PS tests and demonstrates $ED_{50}$ values equal to or more potent than camptothecin itself. 10,11-MDO-20(S)-CPT is also very potent in the L-1210 leukemia in vivo life prolongation assay. The synthesis of 10,11-MDO-20(RS)-CPT is known and described in Wani et al, J. Med. Chem., 29 (11), 2358-2363 (1986) and in U.S. Pat. No. 4,894,456.

Novel analogs of camptothecin have been prepared, all of which contain the 10,11-methylenedioxy moiety. The structures of these compounds are shown below.

In the structure shown above, R is $NO_2$, $NH_2$, $N_3$, hydrogen, halogen (F, Cl, Br, I), COOH, OH, O—$C_{1-3}$ alkyl, SH, S—$C_{1-3}$ alkyl, CN, $CH_2NH_2$, NH—$C_{1-3}$ alkyl, $CH_2$—NH—$C_{1-3}$ alkyl, N($C_{1-3}$ alkyl)$_2$, $CH_2N(C_{1-3}$ alkyl)$_2$, O—, NH— and S—$CH_2CH_2N(CH_2CH_2OH)_2$, $CH_2CH_2CH_2N(CH_2CH_2H)_2$, O—, NH— and S—$CH_2CH_2N(CH_2CH_2CH_2OH)_2$, O—, NH— and S—$CH_2CH_2CH_2N(CH_2CH_2CH_2OH_2)_2$, O—, NH— and S—$CH_2CH_2CH_2N(C_{1-3}$ alkyl)$_2$, O—, NH— and S—$CH_2CH_2CH_2N(C_{1-3}$ alkyl)$_2$, CHO or $C_{1-3}$ alkyl.

Preferred compounds are those in which R is halogen, nitro or amino. The compound in which R is a chlorine atom is particularly preferred.

Z in the structure shown above is H or $C_{1-8}$ alkyl with the proviso that R and Z are not both hydrogen. Preferably, Z is H.

The structure shown above is understood to represent all isomers having the chemical structure indicated. The structure shown above, therefore, represents both 10,11-MDO-20(S)-CPT and 10,11-MDO-20(RS)-CPT compounds.

Compounds having the structure shown above are generally prepared by first synthesizing 10,11-MDO-20(S)-CPT or 10,11-MDO-20(RS)-CPT in which Z is hydrogen or $C_{1-8}$ alkyl. The synthesis of 10,11-MDO-20(RS)-CPT compounds in which Z is hydrogen or $C_{1-8}$ alkyl is possible by means of a Friedlander condensation reaction between an appropriately substituted tricyclic compound representing rings C, D and E of the camptothecin structure with an ortho-amino benzaldehyde or ketone. Friedlander condensation with an ortho-amino benzaldehyde produces compounds in which Z is hydrogen. Condensation using corresponding ortho-amino ketones produces compounds in which Z is $C_{1-8}$ alkyl Synthesis of the 10,11-MDO- 20(RS)-CPT is fully described in U.S. Pat. No. 4,894,456 incorporated herein by reference for a complete description of the synthesis of this starting compound. The synthesis of 10,11-MDO-20(S)-CPT is described in U.S. application serial No. 07/511,953. This application is incorporated herein by reference to provide a complete description of the synthesis of the 10,11-MDO-20(S)-CPT starting compounds in which Z is hydrogen or $C_{1-8}$ alkyl.

The 9-substituted-10,11-MDO-20(RS)-CPT and 9-substituted-10,11-MDO-20(S)-CPT compounds of the present invention can be synthesized from the 10,11-MDOCPT starting materials described above by preparing a diazonium salt at the 9-position. To prepare the diazonium salts, 10,11-MDO-20(S)-CPT or 10,11-MDO-20(RS)-CPT is nitrated to form the corresponding 9-nitro compound. This nitro compound is then reduced to form the corresponding 9-amino compound which is used to prepare the diazonium salt.

Using known mixtures of $H_2SO_4$ and $HNO_3$ and standard nitration reaction conditions for the nitration of camptothecin (CPT) itself, one obtains a mixture of the 12-nitro and 9-nitro-camptothecin analogs with the 12-nitro analog present in considerable excess. A structure analysis of 10,11-MDO-20(S)-CPT and 10,11-MDO-20(RS)-CPT reveals that the 9- and 12-positions are available for nitration and the 10,11-methylenedioxy group appears to exhibit an analogous electronic influence on both the 9- and 12-positions. An analysis of the electronic and steric environments on the potential nitration positions of 10,11- leads to the expectation that both 10,11-MDO-20(S)-CPT and 10-11-MDO-20(RS)-CPT will nitrate in a manner similar to camptothecin itself and provide an excess of the 12-nitro analog. Quite unexpectedly, it was found that nitration of 10,11-MDO-20(S)-CPT and 10,11-MDO-20(RS)-CPT gives substantially the 9-nitro-10,11-MDO-analogs with only trace amounts of the 12-nitro-10,11-MDO analogs. The present method, therefore, provides a surprisingly effective procedure for preparing the 9-nitro-10,11-MDOCPT analogs in high yield regioselectively.

The nitration reaction may be conducted using standard conditions for the nitration of aromatic compounds, and is generally conducted by dissolving/suspending the 10,11-MDOCPT in concentrated sulfuric acid with cooling and stirring followed by the addition of a slight excess of concentrated nitric acid. After stirring for a period of time sufficient to substantially complete the reaction, the solution is poured into water, ice or a ice/water mixture to provide the desired 9-nitro-10,11-MDOCPT compound. Purification can be effected by standard extraction and recrystallization processes.

The 9-nitro-10,11-MDOCPT may then be catalytically reduced using hydrogen and a hydrogenation catalyst such as platinum, palladium, etc., or other conventional hydrogenation reactions. Preferably, the hydrogenation catalyst is present on an inert support such as powdered carbon. Reduction of the 9-nitro analog to the 9-amino analog is conducted using standard hydrogenation solvents and hydrogen pressure conditions. Generally, the nitro compound is dissolved/suspended in ethanol and contacted with a hydrogen atmosphere. The concentration of catalyst and of the nitro compound in the solvent is not critical. Concentrations of the nitro compound from about 1 mg/ml to 3 mg/ml may be used with catalyst concentrations ranging from about 20–100 wt. %. The preferred solvent is absolute ethanol although other conventional inert solvents may be used.

The hydrogenation reaction is generally conducted at ambient temperature although temperatures above or below ambient temperature may be used so long as the camptothecin analog is not decomposed. Hydrogenation reaction times vary with the amount of nitro compound to be hydrogenated and can be easily determined by one skilled in the art. Generally, reaction times ranging from 2-30 hours are sufficient to hydrogenate 9-nitro-10,11-MDOCPT.

Although catalytic hydrogenation is a preferred reduction method, other known chemical reductions such as $FeSO_4/NH_4OH$, Sn/HCl, etc. may also be employed to reduce the nitro group to an amino group.

The formation of diazonium salts is a general reaction undergone by primary aromatic amines upon treatment with sodium nitrite in acidic solution. Accordingly, the 9-amino-10,11-MDOCPT can be treated with sodium nitrite in acid solution to form the corresponding diazonium salt. These diazonium salts are then reacted with nucleophiles or free radicals to generate nitrogen gas ($N_2$) and the desired 9-substituted-10,11-MDOCPT compound. The overall reaction sequence is shown in scheme 1 below. In the scheme, the diazonium salt is shown as structure II where the counter anion X is derived from the acid HX.

Scheme I

Non-limiting examples of suitable acids and reaction conditions to prepare a variety of 9-substituted-10,11-MDOCPT compounds are shown in Table A.

TABLE A

| Example | Reactant | HX | Other Reagents and Conditions | R in Product III |
|---|---|---|---|---|
| 2 | I | HBr | CuBR 80° C. | Br |
| 3 | I | HCl | CuCl 80° C. | Cl |
| 4 | I | HBF$_4$ | CO, Pd(OAc)$_2$ NaOAc, MeCN, 25° C. | CO$_2$H |
| 5 | I | HCl | H$_2$C=NOH, CuSO$_4$ Na$_2$SO$_3$, 25° C.; aq. HCl, 80° C. | CHO |
| 6 | I | H$_2$SO$_4$ | 80° C. | OH |
| 7 | I | HCl | CuCN, 10° C. | CN |
| 8 | I | HCl | NaN$_3$, 25° C. | N$_3$ |
| 9 | I | HCl HBF$_4$ | ≧120° C. | F |
| 10 | I | HCl | aq. KI, 100° C. | I |
| 11 | I | HBF$_4$ | NaNO$_2$, Cu° 25° C. | NO$_2$ |
| 12 | I | H$_2$SO$_4$ | H$_3$PO$_2$, −10° C. | H |
| 13 | I | HCl | 1) KCS$_2$OEt, 40° C. 2) KOH | SH |
| 14 | I | HBF$_4$ | (CH$_3$)$_4$Sn, Pd(OAc)$_2$ MeCN, 25° C. | CH$_3$ |

Additional 10,11-MDOCPT compounds can be prepared by further reactions on the compounds shown in Table A or by analogous reactions. For example, the compound in which R is ethyl (C$_2$H$_5$) or propyl (C$_3$H$_7$) can be prepared by a reaction analogous to Example 14 using the reagent (C$_2$H$_5$)$_4$Sn or (C$_3$H$_7$)$_4$Sn in place of (CH$_3$)$_4$Sn. The compounds in which R is CN can be readily reduced by catalytic hydrogenation to obtain the compound in which R is CH$_2$NH$_2$ by hydrogenation processes analogous to the hydrogenation of 9-nitro-10,11-MDOCPT to 9-amino-10,11-MDOCPT discussed above or other known reduction reactions.

Alkylation reactions of compounds in which R is OH, SH, NH$_2$ or CH$_2$NH$_2$ yields compounds in which R is O—C$_{1-3}$ alkyl, S—C$_{1-3}$ alkyl, NH—C$_{1-3}$ alkyl or CH$_2$NH—C$_{1-3}$ alkyl. Dialkylation of the nitrogen-containing substituents is also possible to yield N(C$_{1-3}$ alkyl)$_2$ and CH$_2$N(C$_{1-3}$ alkyl)$_2$ substituents as R. Alkylation may be accomplished, for example, using C$_1$–C$_3$ alkyl halides or tosylates (OTs). Preferred alkyl halides are the C$_1$–C$_3$ alkyl chlorides and bromides. If desired, a base such as a tertiary amine may be added to facilitate the alkylation reaction.

It is possible to incorporate additional nitrogen and oxygen atoms into the substituent R by means of alkylation reactions. For example, alkylation with a reagent having the formula (C$_{1-3}$ alkyl)$_2$N—CH$_2$CH$_2$—X or (C$_{1-3}$ alkyl)$_2$N-CH$_2$CH$_2$CH$_2$—X, where X is halogen or OTs yields the correspondingly alkylated products containing the di-C$_{1-3}$ alkylaminoethyl or di-C$_{1-3}$ alkylaminopropyl group. In a similar manner, introduction of an oxygen atom is possible using alkylating agents having the formula (HOCH$_2$CH$_2$)$_2$N-(CH$_2$)$_{2-3}$—X and (HOCH$_2$CH$_2$CH$_2$)$_2$N-(CH$_2$)$_{2-3}$—X to provide the corresponding diethanolaminoethyl, diethanol aminopropyl, dipropanolaminoethyl and dipropanolaminopropyl groups. It may be necessary to protect the hydroxyl group in these latter alkylating agents using standard hydroxyl protecting groups such as THPO-. These hydroxyl protecting groups can be conveniently removed or deprotected after alkylation by treatment with mild aqueous acid.

It has also been discovered that water-soluble analogs of 10,11-MDOCPT can be prepared by opening the lactone ring of 10,11-MDOCPT compounds to form water-soluble salts. These new derivatives exhibit substantially improved water-solubility and retain a high level of cytotoxicity.

The interaction of pharmaceutical compounds with biological systems is highly specific and intimately related to the three-dimensional structure of a compound and the chemical functionality present on the pharmaceutical compound. It is well known in the pharmaceutical art that structural changes as simple as the use of an opposite enantiomer can result in complete loss of biological activity and in some instances even opposite biological activity. Surprisingly, it has been discovered that it is possible to hydrolyze the lactone ring of 10,11-MDOCPT and yet retain substantial biological activity while also enhancing water-solubility.

The open lactone compounds of the present invention have the structure shown below where R and Z have the same definition as given above for the closed lactone compounds and further Z and R may both be hydrogen.

The water-soluble analogs of the present invention are prepared by hydrolyzing the lactone ring of 10,11-MDOCPT or a 9-substituted-10,11-MDOCPT by utilizing one equivalent of an aqueous alkali metal hydroxide. The hydrolysis is preferably carried out in an aqueous solution. The resulting product is the alkali metal salt of 10,11-MDOCPT or 9-substituted-10,11-MDOCPT in which the lactone ring has been opened to form the corresponding hydroxyl and carboxylate functional groups, as shown below, where M+ is a monovalent metal cation.

Preferred alkali metal hydroxides are potassium hydroxide and sodium hydroxide, with sodium hydroxide being particularly preferred.

Obviously, alkali metal hydroxide concentrations above or below one equivalent may be used in the present process. Concentrations below one equivalent result in incomplete formation of the metal salt.

The incomplete formation of the camptothecin salt provides a convenient purification method. Unreacted camptothecin (closed lactone form) is only slightly soluble in water and can be filtered off from the aqueous solution containing the camptothecin sodium salt in solution. This provides a convenient method for separating and purifying camptothecin salts.

The hydrolysis reaction may be conducted at any temperature which allows adequate reaction of the 10,11-MDOCPT and alkali metal hydroxide so long as the temperature is sufficiently low to prevent decomposition of the starting materials. Suitable temperatures are from about 5°-50° C. with preferred temperatures being approximately room temperature.

In the hydrolysis reaction, the 10,11-MDOCPT is generally, but not necessarily suspended in a suitable solvent such as methanol or aqueous methanol and treated with aqueous alkali metal hydroxide. To increase the rate of reaction, the reaction mixture may be gently heated. After cooling, the 10,11-MDOCPT metal salt may be isolated by standard recrystallization or chromatographic processes following removal of the methanol and water solvents. Any water miscible solvent conventionally used with camptothecin analogs may be used instead of methanol.

Alkali metal salts (open lactone compounds) of other 10,11-MDOCPT analogs such as 9-substituted-10,11-MDOCPT compounds may also be prepared by analogous reactions. For example, 9-nitro-10,11-MDOCPT, 9-amino-10,11-MDOCPT, 9-chloro-10,11-MDOCPT, 9-amido-10,11-MDOCPT or any other 9-substituted-10,11-MDOCPT derivative may also be hydrolyzed by a process analogous to the process described above for 10,11-MDOCPT to provide the corresponding monovalent metal salts of these derivatives.

Water-soluble derivatives of 10,11-MDOCPT can also be prepared by reacting the amino group of 9-amino-10,11-MDOCPT with appropriately protected amino acids and peptides, $C_{4-10}$ saturated or unsaturated carboxylic acid anhydrides, or the corresponding ester-acid halide derivatives. For example, 9-amino-10,11-MDOCPT may be reacted with the carboxylic acid group of an α-amino acid to give compounds having the structure shown below:

in which Z is as defined above and R is the group —NHCOCHR$^1$NR$^2$R$^3$, where R$^1$ is the side-chain of an α-amino acid, preferably the side chain of a D or L-isomer of one of the naturally occurring amino acids, preferably one of the 20 commonly occurring amino acids, and R$^2$ and R$^3$ are, independently, hydrogen or a lower alkyl group having 1-6 carbon atoms. Additionally, R$^3$ may be a peptide unit containing 1-3 amino acid units bonded to the nitrogen atom through a peptide bond. These water-soluble analogs, therefore, contain from 1-4 peptide units bonded to the 9-amino nitrogen atom by means of a peptide bond. Obviously, amino acids which are not naturally occurring may also be used to prepare water-soluble 9-amido-10,11-MDOCPT derivatives so long as the amino acid has a carboxylic acid, acid halide or other reactive acyl functionality to form the required peptide bond with the 9-amino group of 9-amino-10,11-MDOCPT. Other, preferred side chains R$^1$ are alkyl and aralkyl groups containing 2-20, preferably 2-10 carbon atoms.

Generally, these amino acid and peptide-containing derivatives are prepared using amino acids and peptides in which reactive functional groups such as amino groups and carboxylic acid groups are protected using standard amino acid and carboxylic protecting groups. For example, when preparing a derivative from an amino acid such as glycine, one can protect the amino group of glycine by reaction with tBOC chloride to prepare the reactive tBOC-protected amino acid. Appropriately protected amino acids are also available commercially. The protected amino acid is reacted with 9-amino-10,11-MDOCPT and the tBOC group is then removed to give the water-soluble salt of the 9-glycinamido derivative, for example.

If desired, free amino groups on the amino acids or peptides may be derivatized by known nitrogen alkylation reactions, i.e., reaction with alkyl halides, to provide mono or dialkylamino acid amido derivatives as shown above (R$^2$ and/or R$^3$=alkyl). Preferably, free amino groups are derivatized to form $C_{1-3}$ mono or dialkylamino groups.

Dibasic amino acids such as arginine, histidine, lysine, etc., and dicarboxylic amino acids such as aspartic acid, glutamic acid, etc., may be used for one or more of the amino acids in the amino acid or peptide derivatives described above. If desired, standard addition salts may be prepared by reacting the free amino groups of any amino acid with a mineral acid such as HCl, HBr, $H_3PO_4$ or organic acids such as malic, maleic or tartaric acids. Likewise, free carboxylic acid groups on any amino acid may be derivatized by the formation of monovalent metal cation salts, ammonium salts or quaternary ammonium salts by the addition of monovalent metal hydroxides, ammonia or amines. Quaternary ammonium salts may be formed with primary, secondary or tertiary amines in which the nitrogen atom of the amine contains 1, 2 or 3 lower alkyl or substituted lower alkyl groups. Substituted lower alkyl groups containing one or more hydroxyl groups are preferred. Sodium salts, triethylammonium and triethanol ammonium salts are particularly preferred.

Other water-soluble derivatives can also be prepared by reacting 9-amino-10,11-MDOCPT with a $C_{4-10}$ saturated or unsaturated acid anhydride, the corresponding ester-acid halide or other reactive acyl derivatives to provide analogs having structure I in which R is NHCO—$C_{2-8}$-alkylene—X and NHCO—$C_{2-8}$-alkenyalene—X where X=COOH. The reaction is optionally carried out in a suitable solvent and produces the corresponding half acid. For example, reaction of 9-amino-10,11-MDOCPT with glutaric anhydride gives the 9-glutaramide half acid. Likewise, reaction of 9-amino-10,11-MDOCPT with the $C_{1-6}$ ester-acid halide corresponding to glutaric anhydride results in the 9-glutaramide half acid ester. Conventional hydrolysis of the ester produces the half acid. Water solubility may be imparted in each case by reaction with one equivalent of any of the bases noted above.

The reaction of 9-amino-10,11-MDOCPT with the anhydride or other reactive acyl compound is preferably carried out in the presence of a weak base such as a tertiary amine to facilitate the formation of the product amide. Suitable amines include cyclic amines such as pyridine as well as lower alkyl tertiary amines.

The free acid group of the amide half acid may be further coupled with a suitable alkylene diamine (NHR$^2$—(CH$_2$)$_n$—NR$^2$R$^3$) to give amino amides in which the R group in structure I is —NH— A'—NR$^2$—(CH$_2$)$_n$—NR$^2$R$^3$, where n=1-10, preferably 2-6, and A' is a $C_{4-10}$ acyl-alkylene-acyl or $C_{4-10}$ acyl-alkenylene-acyl group, i.e., R is NHCO—$C_{2-8}$-alkylene—X or NHCO—$C_{2-8}$-alkenylene—X where X is COOH or CONR$^2$—(CH$_2$)$_n$—NR$^2$R$_3$. For example, the reaction of 9-glutaramido-10,11-MDOCPT with a suitable diamine such as 3-(dimethylamino)-1-propylamine gives the corresponding amino acid amide as shown below.

10,11-MDOCPT-NHCO(CH$_2$)$_3$COOH +

Acid and base addition salts of these derivatives may also be prepared in a manner analogous to that described above.

In another embodiment, water-soluble urea and urethane analogs can be prepared by reacting 9-amino-10,11-MDOCPT with phosgene followed by reaction with an appropriate diamine or tertiary-amino alcohol to give compounds having the formula I in which R is —NHCO—B—(CH$_2$)$_n$—NR$^2$R$^3$, where B is oxygen or NH, and compounds in which R is where m+y=3-6 and n, R$^2$ and R$^3$ are as defined above.

Suitable diamines are primary and secondary straight-chain, branched or cyclic diamines containing 3–15 carbon atoms. Examples of straight-chained and branched diamines include diaminoethane, 1,2- and 1,3-diaminopropane, 1,4-diaminobutane, etc. Examples of cyclic diamines included pyrazolidine, imidazolidine, piperazine, etc. Preferred diamines are diamines in which one of the amino groups is derivatized to form a di-lower-alkyl-amino group such as, for example, NH$_2$CH$_2$CH$_2$CH$_2$N(CH$_2$CH$_3$)$_2$. The reaction of 9-amino-10,11-MDOCPT with phosgene followed by a diamine is represented below.

Tertiary-amino alcohols for the preparation of urethane analogs include N,N-di-$C_{1-6}$-alkylamino alkanols prepared from straight chain or branched amino alkanols having 2–10 carbon atoms, for example, N,N-diethyl-aminoethanol.

Water soluble standard acid and base addition salts can be prepared from the urea and urethane analogs in a manner similar to that described above for other amino and carboxylic acid group-containing analogs.

Preferred derivatives within the scope of the present invention are 10,11-MDOCPT analogs having glycinamido, succinamido, glutaramido, (4-methylpiperazino) carbonylamino, N,N-dimethylaminopropylamido-glutaramido and (N,N-diethylaminoethoxy)carbonylamino substituents at the 9-position and the water soluble salts thereof.

The salts of the present invention exhibit substantially improved water-solubility relative to conventional camptothecin analogs and may be formulated into solid and aqueous pharmaceutical compositions by conventional methods. The compounds of the present invention are active in standard cytotoxicity tests and are inhibitors of topoisomerase I.

The 10,11-methylenedioxy (MDO) group confers striking and unexpected improvements on the in vitro and in vivo activity found in the camptothecin molecule with particular reference to anti-tumor activity. Thus, Jaxel et al., Cancer Res., 49, 1465–1469 (1989), and Hsiang et al., Cancer Res., 49, 4385–4389 (1989), have shown that 10,11-MDO-20(RS)-CPT has three to five times the potency of camptothecin in the inhibition of topoisomerase I. Inhibition of this enzyme has been shown by Jaxel et al. (loc. cit.) to be very well correlated with in vivo anti-tumor and anti-leukemic activity.

Figure 1:
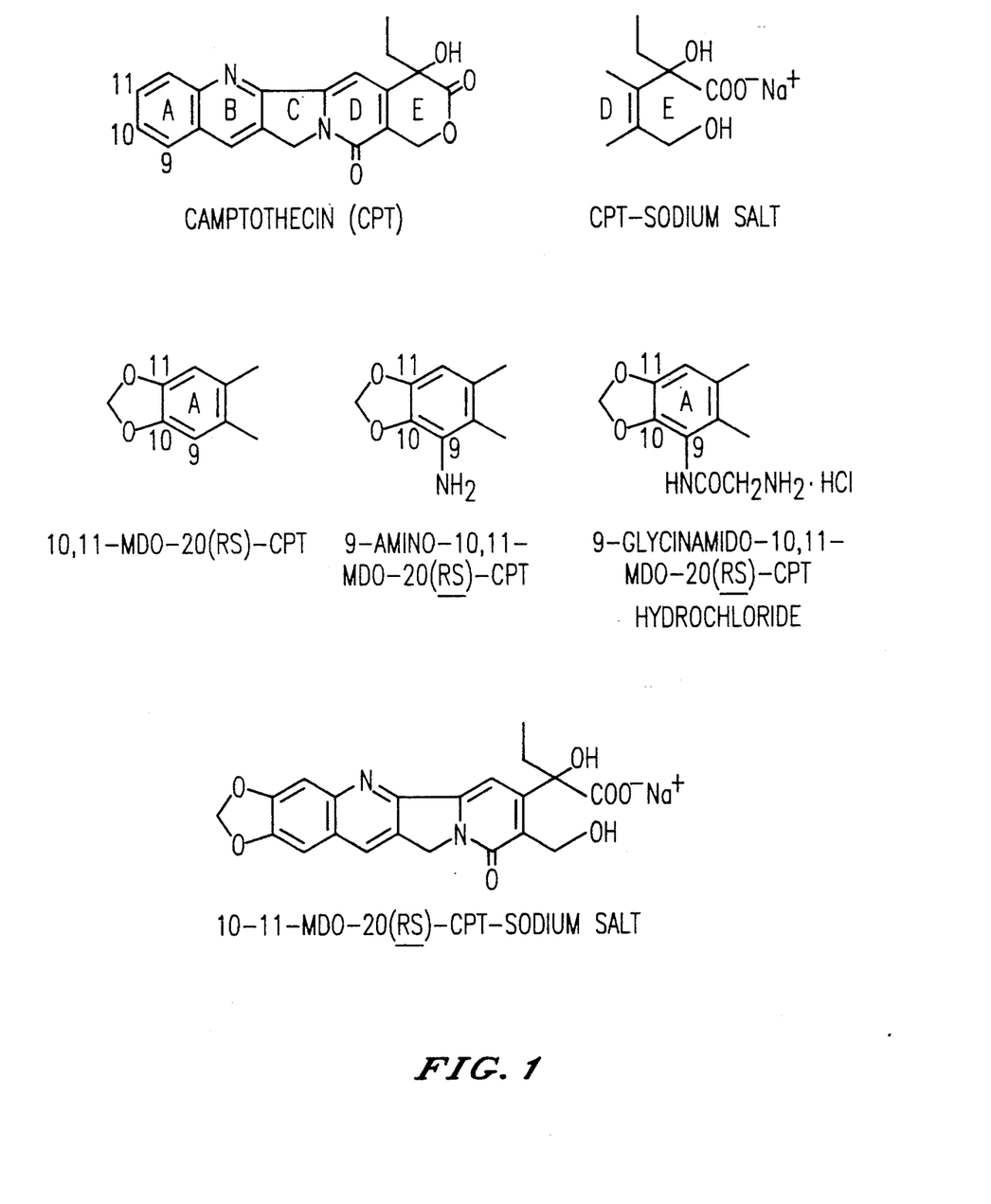
FIG. 1 shows the structure of CPT and derivatives thereof.

In contrast, a compound with quite similar structure, 10,11-dimethoxy-20(RS)-CPT, is totally inactive, Wani et al., *J. Med. Chem.*, 92: 2360 (1986). Unlike 10,11-dimethoxy-20(RS)-CPT, the 10,11-MDO moiety is held rigidly in the plane of ring A of CPT (See the structure in FIG. 1), and this is thought to contribute to the additional biological activity unexpectedly noted with all of these compounds.

Table B shown below shows the potent topoisomerase I inhibitory activity of the compounds of the present invention. The cleavable complex assay was performed according to the method described in Hsiang, Y-H. et al., *J. Biol. Chem.*, 260:14873–14878 (1985). The cleavable complex assay correlates well with in vivo anti-tumor activity in animal models for camptothecin analogs. See Hsiang et al., *Cancer Research*, 49:4385–4389 (1989) and Jaxel et al., *Cancer Research*, 49:1465–1469 (1989).

TABLE B

| Compound | Name* | $EC_{50}$** $\mu g/mL$ |
|---|---|---|
| 1 | 9-AMINO-10,11-MDO-20(S)-CPT | ~.01 μg/mL |
| 2 | 10,11-MDO-20(S)-CPT | ~.01 μg/mL |
| 3 | 10,11-MDO-20(RS)-CPT | ~.02 μg/mL |
| 4 | 9-AMINO-10,11-MDO-20(RS)-CPT | ~.02 μg/mL |
| 5 | 9-NITRO-10,11-MDO-20(RS)-CPT | ~.09 μg/mL |
| 6 | 10,11-MDO-20(S)-CPT, Na+ SALT | ~0.1 μg/mL |
| 7 | 9-GLA-10,11-MDO-20(RS)-CPT, HCl | ~0.1 μg/mL |
| 8 | 10,11-MDO-20(RS)-CPT, Na+ SALT | ~0.2 μg/mL |
| 9 | 20(S)-CPT | ~0.2 μg/mL |
| 10 | 20(RS)-CPT | ~0.8 μg/mL |
| 11 | 20(RS)-CPT, Na+ SALT | ~0.9 μg/mL |
| 12 | 9-AMINO-10,11-MDO-20(S)-CPT, Na+ SALT | ~1 μg/mL |
| 13 | 9,10-MDO-20(RS)-CPT | ~2 μg/mL |
| 14 | 9-AMINO-10,11-MDO-20(RS)-CPT, Na+ SALT | ~2 μg/mL |
| 15 | 9-AMINO-10,11-MDO-20(R)-CPT | >10 μg/mL |
| 16 | 20(R)-CPT | >10 μg/mL |

*Abbreviations
CPT = Camptothecin
MDO = Methylenedioxy
GLA = Glycinamido
**$EC_{50}$ is the concentration of a compound which gives 50% topoisomerase I inhibition as revealed by cleavable complex formation. All $EC_{50}$ values represent the mean of several independent assays; all values are normalized with respect to #9, 20(S)-CPT, which was always assayed as a control.

The present compounds are active against murine tumors, such as lymphocytic leukemia L-1210, RAW117-H10 lymphosarcoma and K1735-M2 melanoma. Activity in one or more of these tumor tests has been reported to be indicative of anti-tumor activity in man (A. Goldin et al., in *Methods in Cancer Research*. ed. V. T. DeVita Jr. and H. Busch, 16: 165, Academic Press, New York, 1979).

In tumor histioculture studies (See Table C) using human cancers obtained by surgery or biopsy, the compounds of the present invention demonstrate significant activity, measured as inhibition of tumor cell proliferation during treatment with the compounds of the present invention. As used herein, the term "cancer" is synonymous with the terms "malignant tumor" and more generally "tumor". The data shown in Table C demonstrate the activity of the present compounds against human colon cancer, which is well known to be a very resistant cancer to chemotherapy. See H. L. Davis, Chemotherapy of Large Bowel Cancer, Cancer (Phila.) 50: 2638-2646 (1982); J. R. Neefe and P. S. Schein, Chapter 43: The Management of Disseminated Large-Bowel Cancer in *Principals of Cancer Treatment*, page 402, ed. S. K. Carter, E. Glatstein and R. B. Livingston, McGraw-Hill Co., 1982; K. Mekhail-Ishak, Cancer Research, 49: 4866–4869 (1989) and P. J. Ferguson and Y. C. Cheng, Cancer Research, 49: 1148–1153 (1989).

TABLE C

HUMAN COLON TUMOR HISTIOCULTURE
Inhibition of Cell Proliferation

| Name* | **$IC_{50}$ (μg/mL) |
|---|---|
| 20(S)-CPT | ~0.02 |
| 10,11-MDO-20(S)-CPT | ~0.003 |
| 10,11-MDO-20(S)-CPT, Na+ SALT | ~0.005 |
| 9-NH$_2$-10,11-MDO-20(S)-CPT | ~0.002 |
| 10,11-MDO-20(RS)-CPT | ~0.005 |
| 10,11-MDO-20(RS)-CPT, Na+ SALT | ~0.01 |
| 9-NH$_2$-10,11-MDO-20(RS)-CPT | ~0.005 |
| 9-NH$_2$-10,11-MDO-20(RS)-CPT, Na+ SALT | ~0.01 |

*Abbreviations
CPT = Camptothecin
MDO = Methylenedioxy
**$IC_{50}$: concentration of compound required to inhibit by 50% the incorporation of $^3$[H]thymidine into DNA
Inhibition of tumor cell proliferation was performed in vitro on human colorectal tumors obtained from surgery or biopsy, as described by Vescio et al (Proc. Nat'l. Acad. Sci. USA 84:5029-5033, 1987) with the following modificiations: Tumors were cultured 1 day prior to drug addition; tumors were exposed to compounds for 24 hours, washed, and then exposed to $^3$[H]thymidine for 3 days.

The compounds of the present invention exhibit anti-tumor activity against human colon cancer, which is known to exhibit de novo drug resistance, and thus be difficult to treat chemotherapeutically. Therefore, it is believed that the present compounds will be active against a wide spectrum of mammalian (including human) cancers such as cancers of the oral cavity and pharynx (lip, tongue, mouth, pharynx), esophagus, stomach, small intestine, large intestine, rectum, liver and biliary passages, pancreas, larynx, lung, bone, connective tissue, skin, breast, cervix uteri, corpus endometrium, ovary, prostate, testis, bladder, kidney and other urinary tissues, eye, brain and central nervous system, thyroid and other endocrine gland, leukemias (lymphocytic, granulocytic, monocytic), Hodgkin's disease, non-Hodgkin's lymphomas, multiple myeloma, etc. Obviously, the present compounds may be used to treat other cancers not specifically named so long as antitumor activity is demonstrated by the present compounds in the particular cancer.

The present invention also includes pharmaceutical compositions containing the camptothecin derivatives of the present invention. There may be included as part of the composition pharmaceutically acceptable binding agents, carriers and/or adjuvant materials. The active materials can also be mixed with other active materials which do not impair the desired action and/or supplement the desired action. The active materials according to the present invention can be administered by any route, for example, orally, parenterally, intravenously, intradermally, subcutaneously, or topically, in liquid or solid form.

For the purposes of parenteral therapeutic adminis-, tration, the active ingredient may be incorporated into a solution or suspension. The solutions or suspensions may also include the following components: a sterile diluent such as water for injection, saline solution, fixed oils, polyethylene glycols, glycerine, propylene glycol or other synthetic solvents; antibacterial agents such as benzyl alcohol or methyl parabens; antioxidants such as ascorbic acid or sodium bisulfite; chelating agents such as ethylenediaminetetraacetic acid; buffers such as acetates, citrates or phosphates and agents for the adjustment of tonicity such as sodium chloride or dextrose. The parenteral preparation can be enclosed in ampoules, disposable syringes or multiple dose vials made of glass or plastic.

Another mode of administration of the compounds of this invention is oral. Oral compositions will generally include an inert diluent or an edible carrier. They may be enclosed in gelatin capsules or compressed into tablets. For the purpose of oral therapeutic administration, the aforesaid compounds may be incorporated with excipients and used in the form of tablets, troches, capsules, elixirs, suspensions, syrups, wafers, chewing gums and the like.

The tablets, pills, capsules, troches and the like may contain the following ingredients: a binder such as microcrystalline cellulose, gum tragacanth or gelatin; an excipient such as starch or lactose, a disintegrating agent such as alginic acid, Primogel, corn starch and the like; a lubricant such as magnesium stearate or Sterotes; a glidant such as colloidal silicon dioxide; and a sweetening agent such as sucrose or saccharin or flavoring agent such as peppermint, methyl salicylate, or orange flavoring may be added. When the dosage unit form is a capsule, it may contain, in addition to material of the above type, a liquid carrier such as a fatty oil. Other dosage unit forms may contain other various materials which modify the physical form of the dosage unit, for example, as coatings. Thus tablets or pills may be coated with sugar, shellac, or other enteric coating agents. A syrup may contain, in addition to the active compounds, sucrose as a sweetening agent and certain preservatives, dyes and colorings and flavors. Materials used in preparing these various compositions should be pharmaceutically pure and non-toxic in the mounts used.

As known in this art, dosage values will vary with the specific cancer to be treated, the stage of tumor development, tumor location, weight and physical condition of the patient being treated, etc. Good results should be achieved when the compounds described herein are administered to a subject requiring such treatment as an effective oral, parenteral or intravenous dose of from about 0.1 to about 100 mg per day per patient. It is to be understood, however, that for any particular subject, specific dosage regimens should be adjusted to the individual need in view of the patients response to treatment with the drug and the professional judgment of the person administering or supervising the administration of the aforesaid compound. It is to be further understood that the dosages set forth herein are exemplary only and they do not limit the scope or practice of the invention. Dosages above or below the range cited above are within the scope of the present invention and may be administered to the individual patient if desired and necessary. The dosages may be administered at once, or may be divided into a number of smaller doses to be administered at varying intervals of time.

Other features of the invention will become apparent from the following descriptions of preferred embodiments which are given for illustration of the invention and are not intended to be limiting thereof.

EXAMPLES

Example 1

Synthesis of 9-Amino-10,11-MDOCPT 10,11-MDO-20(RS)-CPT and 10,11-MDO-20(S)-CPT were prepared according to Wani et al., *J. Med. Chem.*. 29. 2358 (1986) and the process disclosed in U.S. application Ser. No. 07/511,953.

Conversion of 10,11-MDOCPT to 9-Nitro-10,11-MDOCPT 10,11-MDOCPT (332 mg, 0.847 mmol) was dissolved/suspended in conc. $H_2SO_4$ (5 mL), stirred and cooled to 0° C., and treated over 5 min with conc. $HNO_3$ (25 drops). After 1 hr. the brown solution was poured onto ice/$H_2O$ (50 mL) to provide a yelloworange precipitate which was collected by filtration (292 mg). Extraction of the filtrate with $CHCl_3$ (2×50 mL) provided additional material (83 mg) for a total yield of 375 mg (100%). Recrystallization from MeOH/$CHCl_3$ provided a 75% recovery of the title compound as a yellow powder: mp darkening above 255° C. with no melting below 350° C.: IR $\nu_{max}$ (KBr) 3430 (br), 2920, 1741 (lactone), 1654 (pyridone), 1596 (aromatic), 1525 ($NO_2$), 1450, 1343, 1242, 1191, 1154, 1043, 928, 785 and 565 $cm^{-1}$; $^1H$ NMR (DMSO-$d_6$) δ0.87 (t, 3, J=7 Hz, H-18), 1.85 (m, 2, H-19), 5.21 (s, 2, H-5), 5.41 (s, 2, H-17), 6.52 (s, 2, —$OCH_2O$—), 7.24 (s, 1, H-14), 7.78 (s, 1, H-12), 8.96 (s, 1, H-7).

Conversion of 9-Nitro-10,11-MDOCPT to 9-Amino-10,11-MDOCPT

A suspension of the nitro compound (139 mg) prepared above and 10% Pd/C (75 mg) in abs EtOH (40 mL) was stirred at ambient temperature under 1 atm $H_2$ for 20 hr. The mixture was filtered (Celite) and the pad washed profusely with MeOH/$CHCl_3$ and HCl. Evaporation of the solvents afforded the crude amine as an orange-brown solid (125 mg, 97%). Recrystallization from MeOH/$CHCl_3$ gave the title compound as a tan-orange powder (87 mg, 67%), mp darkening above 250° C. with no discreet melting below 350° C. $^1H$ NMR (DMSO-$d_6$) δ0.88 (t, 3, J=7 Hz, H-18), 1.87 (m, 2, H-19), 5.22 (s, 2, H-5), 5.41, (s, 2, H—17), 5.74 (s, 2, $NH_2$), 6.18 (s, 2, -$OCH_2O$—), 6.47 (s, 1, OH), 6.91 (s, 1, H-14), 7.23 (s, 1, H-12), 8.74 (s, 1, H-7).

Example 2

Synthesis of 9-Bromo-10,11-MDO-20(S)-CPT (III, R=Br)

A stirred mixture of 9-amino-10,11-MDO-20(S)-CPT (10.0 mg, 25.5 μmol) in 48% aq HBr (0.5 mL) at 0° C. was treated with a solution of $NaNO_2$ (2.1 mg, 30.6 μmol) in $H_2O$ (25 μl). The cooling source was removed, and after the addition of CuBr (4.0 mg, 35 μmol), the brown mixture was heated for 20 min at 80° C. The mixture was cooled and poured over ice (3 g). The resulting suspension was extracted with several 10 mL portions of $CHCl_3$, and the extract was dried ($Na_2SO_4$) and evaporated under reduced pressure to afford an orange-yellow solid (10 mg) containing mostly the title compound III (R=Br) and, to a lesser extent, III (R=H). Purification was effected by flask column (1 g 230-400 mesh $SiO_2$, 0.25-1% MeOH in $CHCl_3$) to provide III (R=Br) as a pale yellow solid (3.8 mg) and III (R=H) in later fractions as a cream colored solid (2.0 mg). 300 MHz $^1$H NMR (DMSO-d$_6$) δ0.84 (t, 3, J=7 Hz, H-18), 1.82 (m, 2, H-19), 5.24 (s, 2, H-5), 5.39 (s, 2, H-17), 6.36 (s, 2, —OCH$_2$O—), 6.49 (s, 1, OH), 7.24 (s, 1, H-14), 7.54 (s, 1, H-12), and 8.63 (s, 1, H-7̄); HRMS: calcd. for C$_{21}$H$_{15}$N$_2$O$_6$Br, 470.0114; measured, 470.0115.

Example 3

Synthesis of 9-Chloro-10,11-MDO-20(S)-CPT (III, R=Cl)

The intermediate diazonium chloride II (X=Cl) is prepared as in Example 2 except that 39% aq HCl is used. Similarly, the substitution of CuCl leads to the expected 9-chloro compound III (R=Cl) after chromatography.

Example 4

Synthesis of 9-Carboxy-10,11-MDO-20(S)-CPT (III, R=Co$_2$H)

The diazonium salt II (X=Cl) is prepared as in Example 2. After filtration of the aq HCl solution, aq HBF$_4$ is added to give a precipitate of II (X=BF$_4$). This salt is combined in a pressure reactor with Pd(OAc)$_2$ and NaOAc in MeCN. Carbon monoxide (1-2 atm) is introduced and the mixture is left for 1 hr at ambient temperature. The mixture is concentrated by evaporation and reconstituted in H$_2$O. Crude III (R=CO$_2$H) is isolated by extraction into CHCl$_3$, and purified by further extraction into dilute aq NaHCO$_3$ followed by precipitation with acid.

Example 5

Synthesis of 9-Formyl-10,11-MDO-20(S)-CPT (III, R=CHO)

The diazonium salt II (X=Cl) is prepared as in Example 2. The salt solution is treated at room temperature with an aqueous solution of formaldoxime containing CuSO$_4$ and Na$_2$SO$_3$. After 1 hr, conc. HCl is added and the intermediate oxime is collected and hydrolyzed to the product aldehyde III (R=CHO) by refluxing in conc. HCl.

Example 6

Synthesis of 9-Hydroxy-10,11-MDO-20(S)-CPT (III, R=OH)

The intermediate diazonium salt II (X=HSO$_4$) is prepared in a manner analogous to that of Example 2 by using aq H$_2$SO$_4$ instead of aq HBr. The mixture is then heated at 80° C. for 1 hr whereby hydrolysis occurred. On cooling, the product III (R=OH) is isolated by extraction into CHCl$_3$.

Example 7

9-Cyano-10,11-MDO-20(S)-CPT (III, R=CN)

The diazonium chloride II (X=Cl) is prepared as in Example 2 and treated at 20° C. with CuCN after the pH has been adjusted to 7 with Na$_2$CO$_3$. After 2 hr, the reaction mixture is extracted with CHCl$_3$. The CHCl$_3$ extract is used to isolate the title compound III (R=CN) by chromatography.

Example 8

9-Azido-10,11-MDO-20(S)-CPT (III, R=N$_3$)

The diazonium chloride II (X=Cl) is prepared as described in Example 2. The resulting mixture is treated with an aqueous solution of NaN$_3$, and after 15 min at room temperature, the azide III (R=N$_3$) results as a precipitate. Centrifugation provides the product as a pale solid which is purified by column chromatography.

Example 9

9-Fluoro-10,11-MDO-20(S)-CPT (III, R=F)

The diazonium chloride II (X=Cl) is prepared as before (Example 2), and after filtration the stirred solution is treated at 0° C. with a slight excess of HBF whereupon salt II (X=BF$_4$) precipitates. After collection and drying, this salt is pyrolized ($\geq$120°) over 1 hr to afford fluoro product III (R=F). Dark colored impurities can be removed by a flash column chromatography.

Example 10

9-Iodo-10,11-MDO-20(S)-CPT (III, R=I)

A solution of chloride II (X=Cl, prepared as before, Example 2) in aq HCl is treated with aq KI and heated for 1 hr. Upon cooling, the mixture is extracted with CHCl$_3$, and the extract concentrated and subjected to column chromatography to provide III (R=I).

Example 11

9-Nitro-10.11-MDO-20(S)-CPT (III, R=NO$_2$)

The salt II (X=BF$_4$) is isolated as in Example 4 and treated at 25° with aq NaNO$_2$ solution followed by the addition of copper powder. After 1 hr, the mixture is extracted with CHCl$_3$ which on evaporation gives crude III (R=NO$_2$) Column chromatography affords pure III (R=NO$_2$).

Example 12

10,11-MDO-20(S)-CPT (III, R=H)

The solution of diazonium sulfate II (X=HSO$_4$), prepared as in Example 6, is maintained at $-10°$ to $0°$ and treated with excess hypophosphorous acid (H$_3$PO$_2$). After 1 hr, the unsubstituted product III (R=H) can be isolated in nearly pure form by extraction with a few portions of CHCl$_3$.

Example 13

9-Mercapto-10,11-MDO-20(S)-CPT (III, R=SH)

A diazonium chloride II (X=Cl) solution, prepared as in Example 2, is treated at 40° with potassium ethyl xanthate (KCS$_2$OEt). The intermediate ethyl xanthate is extracted into CHCl$_3$, and after evaporation of the CHCl$_3$, the xanthate is hydrolyzed with KOH in aq MeOH. The solution is neutralized with conc. HCl and the thiol III (R=SH) isolated by extraction with CHCl$_3$.

Example 14

9-Methyl-10,11-MDO-20(S)-CPT (III, R=Me)

The diazonium tetrafluoroborate salt II (X=BF$_4$), prepared as in Example 4, is added to MeCN and to the resulting stirred mixture is added Me$_4$Sn and Pd(OAc)$_2$ at room temperature. After 2 hr, the MeCN is evaporated and the residue partitioned between H$_2$O and CHCl$_3$. The CHCl$_3$ is reserved and the aqueous portion is extracted twice more with CHCl$_3$. From this extract, III (R=Me) is isolated.

Example 15

9-Ethyl-10,11-MDO-20(S)-CPT (III, R=Et)

The diazonium tetrafluoroborate salt II (X=BF$_4$), prepared as in Example 4, is added to MeCN and to the resulting stirred mixture is added Et$_4$Sn and Pd(OAc)$_2$ at room temperature. After 2 hr, the MeCN is evaporated and the residue partitioned between H$_2$O and CHCl$_3$ The CHCl$_3$ is reserved and the aqueous portion is extracted twice more with CHCl$_3$. From this extract, III (R=Et) is isolated.

Example 16

Conversion of 9-Amino-10,11-MDOCPT to 9-Glycinamido-10,11-MDOCPT Hydrochloride

A stirred mixture of the 9-amino compound (186 mg. 0.457 mmol) and BOC-glycine (150 mg, 0.85 mmol) in pyridine (1 mL) and DMF (15 mL) was chilled to 0° C. and treated with DCC (200 mg, 0.971 mmol). The mixture was warmed to ambient temperature and stirred for 65 hr. The solvents were evaporated and the residue dissolved in MeOH/CHC$_3$. Celite (3 g) was added, the mixture evaporated, and the Celite-dispersed sample placed on a silica gel column (20 g). Elution (200 mL CHCl$_3$, 500 mL 5% MeOH/CHCl$_3$, 500 mL 12% MeOH/CHCl$_3$) and evaporation of appropriate fractions gave the intermediate BOC-protected derivative (98 mg , 38%). The derivative was treated with chilled conc HCl/dioxane (1:9, 5 mL), and the resulting mixture was stirred at ambient temperature for 5 hr. The solvent was evaporated, the residue sonicated in deionized H$_2$O (50 mL) and filtered (0.45 micron membrane). The clear yellow solution was lyophilized to give an amber gummy solid which on trituration with abs EtOH gave the glycinamide hydrochloride salt as a yellow microcrystalline solid (57 mg, 73%), mp darkening above 230° C. with no apparent melting below 340° C. IR $\nu_{max}$(KBr) 3680-2300 with maxima at 3220, 2990 and 2920 (OH, amide H, amine HCl), 1740 (lactone), 1700 (amide), 1655 (pyridone), 1585, 1492, 1447, 1390, 1249, 1160, 1108, 1075, 1041, 933 and 845 cm$^{-1}$; $^1$H NMR (DMSO-d$_6$) δ0.89 (t, 3, J=7 Hz, H-18), 1.87 (m, 2, H-19), 4.02 (d, 2, J =5.4 Hz, COCH$_2$N—), 5.17 (s, 2, H-5), 5.42 (s, 2, H-17), 6.32 (s, 2, —OCH$_2$O—), 07.26 (s, 1, H-14), 7.47 (s, 1, H-12), 8.38 (br s, 3,—NH$_3$), 8.59 (s, 1, H-7), 1075 (s, 1, amide H).

Example 17

Synthesis of 9-Glutaramido-10,11-MDOCPT Triethanolamine Salt

A stirred suspension of 9-amino-10,11-MDOCPT and glutaric anhydride in pyridine under nitrogen was heated at 95° C. for 2 hr. The solvent was removed from the brown solution by high vacuum distillation to give the crude amide as a brown gum. Purification was effected by chromatography through silica gel employing a solvent gradient from 5% methanol/chloroform to 50% methanol/chloroform. Evaporation of the appropriate fractions gave the 9-glutaramide half acid.

Alternatively, the 9-glutaramido derivative can be prepared by hydrolysis of its ethyl ester which is prepared by the following general method: 9-Amino-10,11-MDOCPT in dry N,N-dimethylformamide containing pyridine is reacted at 0°-10° C. with a slight excess of ethylglutaryl chloride in N,N-dimethylformamide solution. After work-up and chromatography on silica gel, the 9-(ethyl)glutaramide derivative is obtained.

Example 18

Synthesis of 9-(4-methylpiperazino) carbonylamino-10,11-MDOCPT Hydrochloride

The title compound was prepared from 9-amino-10,11-MDOCPT in the following manner:

9-(4-Methylpiperazino)carbonylamino-10,11-MDOCPT

9-Amino-10,11-MDOCPT was added to chloroform (treated with alumina to remove hydroxylio components) containing triethylamine. The resulting solution was treated with phosgene gas and filtered to remove solids. The filtrate containing the intermediate carbamoyl chloride was treated with N-methylpiperazine under nitrogen and left overnight. The turbid mixture was washed several times with aqueous sodium bicarbonate solution, dried and evaporated to afford the crude title compound. Chromatography on silica gel provided 9-(4-methylpiperazino)carbonylamino-10,11-MDOCPT.

9-(4-Methylpiperazino)carbonylamino-10,11-MDOCPT Hydrochloride

The free base urea obtained above was suspended in methanol and treated with one equivalent of dilute aqueous hydrochloric acid. The methanol was evaporated and the aqueous residue filtered through a membrane filter. The sample was lyophilized to provide the title compound.

Example 19

Synthesis of 9-(N,N-Diethylaminoethoxy) carbonylamino-10,11-MDOCPT

The intermediate 9-carbamoyl chloride was prepared as in the preceding example. The resulting chloroform solution was treated with N,N-diethylaminoethanol under nitrogen. After standing overnight, the mixture was washed with aqueous sodium bicarbonate solution, dried and evaporated to afford the crude carbamate. Purification by silica gel chromatography gave the pure title carbamate as the free base.

Example 20

9-(N,N-Diethylaminoethoxy)carbonylamino-10,11-MDOCPT Hydrochloride

The free base from Example 5 was suspended in methanol and treated with one equivalent of dilute aqueous hydrochloric acid. The methanol was evaporated and the aqueous solution filtered (membrane). Lyophilization afforded the water soluble title carbamate.

Example 21

10,11-MDO-20(RS)-camptothecin Sodium Salt

The title compound was prepared from 10,11-MDO-20(RS)-camptothecin (Wani et al., *J. Med. Chem.* 29, 2358 (1986)) by hydrolytic action of sodium hydroxide. Thus, 10,11-MDO-20(RS)-CPT (77 mg, 0.194 mmol) was suspended in 90% aqueous methanol (30 mL) and treated with 0.1 N aqueous sodium hydroxide (1.94 mL, 0.194 mmol). Upon heating at 50°-60° C. for 1 h under nitrogen a clear solution resulted which was cooled to ambient temperature and evaporated to dryness. The residue was dissolved in distilled water (2 mL) and filtered (0.45 micron membrane), and the resulting solution evaporated. The residue was recrystallized from ethanol/ether to provide the compound as a pale yellow solid (53 mg, 65%), mp>300° C.; IR $\nu_{max}$ (KBr) 3400 (br), 2970, 2920, 1640, 1610, 1560–1580, 1497, 1466, 1370, 1246, 1225, 1183, 1030, 1000, 947, 855, 810, 761, 708 and 560–580; $^1$H NMR (DMSO-d$_6$) δ0.85 (t, 3, J=7 Hz, H-18), 2.09 (m, 2, H-19), 4.74 (ABq, 2, Δν=68 Hz, J=12, 4 Hz, H-17), 5.12 (s, 2, H-5), 5.64 (dd, 1, J=4, 7 Hz, 17-OH), 6.17 (s, 1, 20-OH), 7.47 (s, 1, H-14), 7.54 (s, 1, H-9), 7.62 (s, 1, H-12), 8.41 (s, 1, H-7).

Example 22

9-Amino-10,11-MDO-20(RS)-Camptothecin Sodium Salt

The title compound was prepared by an analogous alkaline hydrolysis of 9-amino-10,11-MDO-20(RS)CPT which was prepared as described above. Thus, a suspension of 9-amino-10,11-MDO-20(RS)CPT in aqueous methanol was warmed with one equivalent of aqueous sodium hydroxide to provide a clear solution. Isolation as above provided the water soluble title compound as an orange-yellow solid.

Obviously, numerous modifications and variations of the present invention are possible in light of the above teachings. It is therefore to be understood that within the scope of the appended claims, the invention may be practiced otherwise than as specifically described herein.

What is claimed as new and desired to be secured by letters patent of the United States is:

1. A 20(S) or 20(RS)-camptothecin having the structure shown below:

wherein Z is hydrogen or $C_{1-8}$ alkyl, R is $NO_2$, $NH_2$, $N_3$, hydrogen, halogen, COOH, OH, O—$C_{1-3}$ alkyl, SH, S—$C_{1-3}$ alkyl, CN, $CH_2NH_2$, NH—$C_{1-3}$ alkyl, $CH_2$—NH—$C_{1-3}$ alkyl, N($C_{1-3}$ alkyl)$_2$, $CH_2N(C_{1-3}$ alkyl)$_2$, O—, NH— or S—$CH_2CH_2N(CH_2CH_2OH)_2$, O—, NH— or S— $CH_2CH_2CH_2N(CH_2CH_2H)_2$, O—, NH— or S—$CH_2CH_2N(CH_2CH_2CH_2OH)_2$, O—, NH— or S—$CH_2CH_2CH_2N(CH_2CH_2CH_2OH)_2$, O—, NH— or S—$CH_2CH_2N(C_{1-3}$ alkyl)$_2$, O—, NH— or S—$CH_2CH_2CH_2N(C_{1-3}$ alkyl)$_2$, CHO, $C_{1-3}$ alkyl or NHCOCHR$^1$NR$^2$R$^3$, where R$^1$ is the side-chain of an α-amino acid and R$^2$ and R$^3$, independently, are hydrogen or a lower alkyl group or R$^3$ is a peptide unit containing 1-3 amino acid units bonded to the nitrogen through a peptide bond; NHCO—$C_{2-8}$-alkylene—X or NHCO—$C_{2-8}$-alkenyalene—X, where X is COOH; CONR$^2$—$(CH_2)_n$—NR$^2$R$^3$, where n=1–10 and R$^2$ and R$^3$ are as defined above; NHCO—B—$(CH_2)_n$—NR$^2$R$^3$, where B=oxygen or NH; or where $m+y=3-6$, with the proviso that R and Z are not both hydrogen, and salts thereof.

2. The camptothecin of claim 1, wherein R is NHCOCHR$^1$NR$^2$R$^3$.

3. The camptothecin of claim 2, wherein R$^1$ is the side chain of a naturally occurring α-amino 4. The camptothecin of claim 2, wherein R$^2$ and R$^3$ are, independently, hydrogen or a lower alkyl group having 1-6 carbon atoms.

5. The camptothecin of claim 2, wherein R$^3$ is a peptide unit containing 1-3 amino acid units.

6. The camptothecin of claim 2, wherein R$^1$ is a $C_{2-20}$ alkyl or aralkyl group.

7. The camptothecin of claim 1, wherein R is NHCO—$C_{2-8}$-alkylene—X or NHCO—$C_{2-8}$-alkenylene—X.

8. The camptothecin of claim 7, wherein X is COOH.

9. The camptothecin of claim 7, wherein X is CONR$^2$—$(CH_2)_n$—NR$^2$R$^3$.

10. The camptothecin of claim 1, wherein R is NHCO—B—$(CH_2)_n$—NR$^2$R$^3$ or where B is oxygen or NH and $m+y=3-6$.

11. The camptothecin of claim 10, wherein B is oxygen and $m+y=3-4$.

12. The camptothecin of claim 10, wherein B is NH and $m+y=3-4$.

13. The camptothecin of claim 1, wherein said salts are mineral acid or organic acid addition salts.

14. The camptothecin of claim 1, wherein said salts are monovalent metal cation salts, ammonium salts or quaternary ammonium salts.

15. The camptothecin of claim 1, wherein R is Cl and Z is H.

16. The camptothecin of claim 1, wherein R is $NH_2$ or $NO_2$ and Z is H.

17. The camptothecin of claim 1, wherein said camptothecin is a 20(S)-camptothecin.

18. A pharmaceutical composition comprising the camptothecin of claim 1 and a pharmaceutically acceptable carrier.

19. A 20(S) or 20(RS)-camptothecin salt, wherein said salt has the structure shown below wherein Z is hydrogen or $C_{1-8}$ alkyl R is $NO_2$, $NH_2$, $N_3$, hydrogen halogen, COOH, OH, O—$C_{1-3}$ alkyl, SH, S—$C_{1-3}$ alkyl, CN, $CH_2NH_2$, NH—$C_{1-3}$ alkyl, $CH_2$—NH—$C_{1-3}$ alkyl, N($C_{1-3}$ alkyl)$_2$, $CH_2N(C_{1-3}$ alkyl)$_2$, O—, NH— or S—CH$_2$CH$_2$N(CH$_2$CH$_2$OH)$_2$, O—, NH— or S— CH$_2$CH$_2$CH$_2$N(CH$_2$CH$_2$OH)$_2$, O—, NH— or S—CH$_2$CH$_2$N(CH$_2$CH$_2$CH$_2$OH)$_2$, O— NH— or S—H$_2$CH$_2$CH$_2$N(CH$_2$CH$_2$CH$_2$OH$_2$$_2$, O—, NH— or S—H$_2$CH$_2$N(C$_{1-3}$ alkyl)$_2$, O—, NH— or S—CH$_2$CH$_2$CH$_2$N(C$_{1-3}$ alkyl)$_2$, CHO, C$_{1-3}$ alkyl or NHCOCHR$^1$NR$^2$R$^3$, where R$^1$ is the side-chain of an α-amino acid and R$^2$ and R$^3$, independently, are hydrogen or a lower alkyl group or R$^3$ is a peptide unit containing 1–3 amino acid units bonded to the nitrogen through a peptide bond; NHCO—C$_{2-8}$-alkylene—X or NHCO—C$_{2-8}$-alkenylene—X, where X is COOH; CONR$^2$—(CH$_2$)$_n$—NR$^2$R$^3$, where n=1–10 and R$^2$ and R$^3$ are as defined above; NHCO—B—(CH$_2$)$_n$—NR$^2$R$^3$, where B=oxygen or NH; or where $m+y=3-6$, M$^+$ is a monovalent metal cation and salts thereof.

20. The camptothecin salt of claim 19, wherein M$^+$ is a sodium cation.

21. The camptothecin salt of claim 19, wherein R is NO$_2$.

22. The camptothecin salt of claim 19, wherein R is NH$_2$.

23. The camptothecin salt of claim 19, where R is H and Z is H.

24. The camptothecin salt of claim 19, wherein said salt is a 20(S)-camptothecin salt.

25. A pharmaceutical composition, comprising the camptothecin salt of claim 19 and a pharmaceutically acceptable carrier.

26. A method for preparing 9-nitro-10,11-methylenedioxy-20(S) or 20(RS)-camptothecin, comprising reacting 10,11-methylenedioxy 20(S) or 20(RS)- camptothecin with a mixture of concentrated sulfuric acid and concentrated nitric acid to obtain a product containing substantially 9-nitro-10,11-methylenedioxy-20(S)— or 20(RS)-camptothecin.

27. A method for preparing 9-amino-10,11 methylenedioxy-20(S)- or 20(RS)-camptothecin, comprising the steps of nitrating 10,11-methylenedioxy-20(S)- or 20(RS)-camptothecin to obtain 9-nitro-10,11-methylenedioxy-20(S)- or 20(RS)-camptothecin, and then reducing the 9-nitro group of said 9-nitro-10,11-methylenedioxy-20(S)— or 20(RS)— or 20(RS)-camptothecin.

28. The method of claim 27, wherein said reducing step is conducted by catalytic hydrogenation.

29. A method of inhibiting the enzyme topisomerase I, comprising contacting said enzyme with an inhibitory amount of the camptothecin of claim 1.

30. A method of inhibiting the enzyme topisomerase I, comprising contacting said enzyme with an inhibitory amount of the camptothecin salt of claim 19.

* * * * *